United States Patent [19]

Urbach et al.

[11] 3,969,389

[45] July 13, 1976

[54] MANUFACTURE OF ALIPHATIC ISOCYANATES

[75] Inventors: Hans Urbach, Lampertheim; Albrecht Mueller, Frankenthal, both of Germany

[73] Assignee: BASF Aktiengesellschaft, Ludwigshafen (Rhine), Germany

[22] Filed: Mar. 3, 1975

[21] Appl. No.: 555,031

[30] Foreign Application Priority Data

Mar. 11, 1974 Germany............................ 2411441

[52] U.S. Cl............................................. 260/453 P
[51] Int. Cl.²...................................... C07C 118/00
[58] Field of Search................... 260/453 P, 453 PH

[56] References Cited
UNITED STATES PATENTS 3,388,145   6/1968   Merz................................... 260/453

Primary Examiner—Lewis Gotts
Assistant Examiner—Dolph H. Torrence
Attorney, Agent, or Firm—Johnston, Keil, Thompson & Shurtleff

[57] ABSTRACT

Aliphatic isocyanates are manufactured by thermal decomposition of aliphatic carbamic acid halides at a temperature not less than 25°C above their boiling points in the presence of higher-boiling organic solvents and subsequent isolation of the resulting aliphatic isocyanate from the decomposition mixture. The isocyanates which may be manufactured by the process of the invention are valuable starting materials for the manufacture of plant protection agents, pesticides, dyes, synthetic resins and plastics, hydrophobic agents for textiles, detergents, bleaches and adhesives.

11 Claims, 1 Drawing Figure

U.S. Patent July 13, 1976 3,969,389
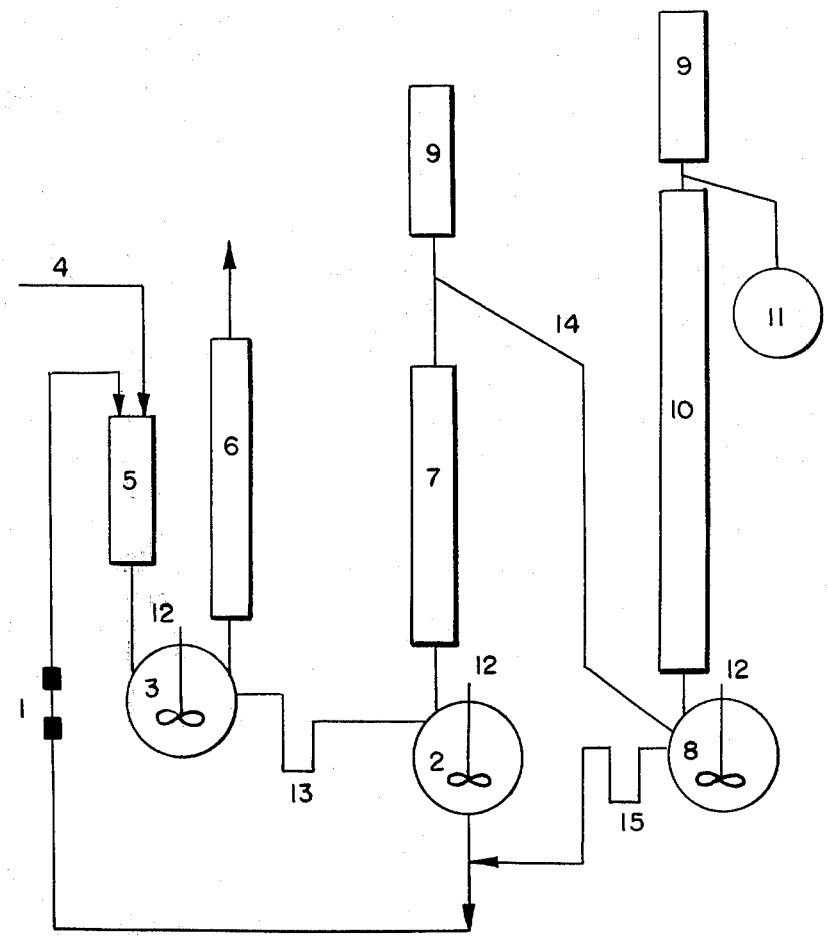

MANUFACTURE OF ALIPHATIC ISOCYANATES

The invention relates to a process for the manufacture of aliphatic isocyanates by thermal decomposition of aliphatic carbamic acid halides at a temperature not less than 25°C above their boiling points in the presence of higher-boiling organic solvents and subsequent isolation of the resulting aliphatic isocyanate from the decomposition mixture.

The manufacture of isocyanates from carbamic acid chlorides in the presence of organic bases such as tertiary amines or N,N-dialkylcarboxylic acid amides (German Published Application No. 1,593,554) in organic solvents is known. Isocyanates can also be obtained by using aqueous solutions or suspensions of inorganic bases, such as alkali metal hydroxides, alkaline earth metal hydroxides, alkali metal carbonates, alkaline earth metal carbonates or alkali metal bicarbonates (British Pat. No. 1,208,862). U.S. Pat. No. 3,465,023 expressly draws attention to the fact that the formation of hydrogen chloride during the manufacture of isocyanates lowers the reactivity of the end products and that therefore it is important to neutralize the acid during the process. There are also difficulties in distilling the isocyanate, and corrosion of the equipment occurs. The above processes have the disadvantage that the isocyanates are formed in a medium in which they are prone to decompose. Thus it is known from Houben-Weyl, Methoden der organischen Chemie, volume 8, page 136 (1952) that isocyanates dimerize in the presence of tertiary amines. They are extremely unstable to aqueous alkali and are substantially converted to carbamates or carbamic acids even if only stoichiometric amounts of aqueous alkali are used.

It is known from German Pat. No. 1,193,034 to decompose N-alkylcarbamic acid chlorides with alkyl groups of 1 to 3 carbon atoms in an organic solvent, the hydrogen chloride formed being removed through a reflux condenser and the alkyl isocyanate formed being removed at the same time from the reaction chamber by distillation through a column. The solvent must boil at least 10°C above the boiling point of the alkyl isocyanate formed. It is pointed out that isocyanates of boiling point below the decomposition temperature of the corresponding carbamic acid chlorides cannot be manufactured by boiling the carbamic acid chlorides under reflux; examples of such isocyanates are alkyl isocyanates. The above patent states that whilst in such cases the carbamic acid chlorides are decomposed thermally an equilibrium is set up and a large part of the hydrogen chloride re-forms the starting material by reaction with the isocyanate formed. To avoid this, alkaline compounds have previously been used to neutralize the hydrogen chloride. Where carbamic acid chlorides with alkyl groups of 1 to 3 carbon atoms are concerned, the patent states that the desired object is achieved by simultaneously removing the isocyanate and the hydrogen chloride from the decomposition chamber.

The claims and the description show that it is not the decomposition temperature of the alkyl compounds but the fact that the boiling point of the solvent is higher than the boiling point of the isocyanate which is essential to the invention. From claim 1 and the description (column 1, last paragraph) it had to be assumed, e.g., that it would be possible to carry out the decomposition even in the presence of an organic solvent boiling below the boiling point of the carbamic acid chloride and at a temperature below this boiling point, provided the above difference in boiling points between the solvent and the isocyanate is adhered to.

Example 1 shows that the simultaneous removal of hydrogen chloride and isocyanate is the decisive factor in achieving satisfactory thermal decomposition of the starting chloride: if a solution of the alkylcarbamic acid chloride is merely boiled under reflux, only 43% of the amount of hydrogen chloride expected are eliminated, if the solution is boiled under a column without at the same time using a reflux condenser, only 20% are eliminated, whilst if the process described in German Pat. No. 1,193,034 is followed, 97% are eliminated. The further examples and the drawing also highlight the importance of simultaneously removing the hydrogen chloride and isocyanate.

It is an object of the invention to provide a new process for the simpler and more economical manufacture of isocyanates, in good yield and high purity.

We have found that aliphatic isocyanates are obtained advantageously by thermal decomposition of aliphatic carbamic acid halides in the presence of inert organic solvents by a method wherein, in a first stage, an aliphatic carbamic acid halide is decomposed at a temperature not less than 25°C above its boiling point in the presence of a solvent which boils at or above this temperature, during which stage the hydrogen halide formed is removed, and then, in a second stage, the aliphatic isocyanate formed is isolated from the reaction mixture.

Where isopropylcarbamic acid chloride is used, the reaction can be represented by the following equation:

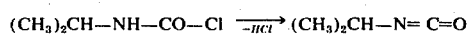

$$(CH_3)_2CH-NH-CO-Cl \xrightarrow{-HCl} (CH_3)_2CH-N=C=O$$

Compared to conventional processes, which use bases to neutralize the acid, the process of the invention gives isocyanates more simply and more economically, in good yield and high purity. Compared to the process described in German Pat. No. 1,193,034, the process of the invention is more reliable and easier to regulate. In industrial operation, the setting, regulating and monitoring of the reaction pressure, particularly during the decomposition of the starting material, are, specifically, greatly facilitated, hence leading to fewer operatives and monitoring personnel being required and to corresponding savings in monitoring instruments. Since the process of the invention is carried out in two stages, the reaction steps are more easily controllable and in each part of the plant only one operation must be controlled and monitored. The elimination and removal of toxic hydrogen halide, in particular, is therefore easy to regulate, and the process is more reliable in operation, and the hazard to operatives is less, than, in particular, in the case of the German patent cited. The difficulties in respect of distillation, corrosion problems and reduction in reactivity of the end products, mentioned in the U.S. patent, do not arise to a significant degree. These advantages are surprising, because the state of the art would have led to the expectation of substantial re-formation of the starting materials from the isocyanate formed and the hydrogen halide. In contrast to the statements of German Pat. No. 1,193,034, these results are achieved by a two-stage process wherein the hydrogen halide must be removed before isolating the end product, and at higher decomposition temperatures, the temperature being set to the decomposition temperature according to the invention, from the very start of the reaction.

Preferred starting materials are those of the formula

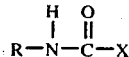
I and correspondingly preferred end products are those of the formula $R - N = C = O$  II wherein R is a saturated aliphatic hydrocarbon radical, preferably alkyl of 1 to 10, especially of 1 to 4, carbon atoms, or an unsaturated aliphatic hydrocarbon radical, preferably alkyl of 2 to 10, especially of 2 to 4, carbon atoms, and X is bromine or preferably chlorine. The above radicals can in addition be substituted by groups and/or atoms which are inert under the reaction conditions, e.g., alkyl of 1 to 5 carbon atoms, alkoxy of 1 to 5 carbon atoms, carbalkoxy, alkenyl of 2 to 5 carbon atoms, or chlorine.

Examples of starting materials I are methyl-, ethyl-, n-propyl-, i-propyl-, n-butyl-, i-butyl-, sec.-butyl-, t-butyl-, 2-methylbutyl-(1)-, 3-methylbutyl-(1)-, 2-methylbutyl-(2)-, 3-methylbutyl-(2)-, pentyl-(1)-, pentyl-(2)-, pentyl-(3)-, neo-pentyl-, n-hexyl-, n-octyl-, chloromethyl-, 2-chloroethyl-, 3-chloropropyl-, 4-chlorobutyl-, 6-chlorohexyl-, 1-chloropropyl-(2)-, 1-chlorobutyl-(2)-, chloro-t-butyl-, bromo-t-butyl-, 1,1-bis-chloromethyl-ethyl-(1)-, tris-chloromethyl-methyl-, allyl-, 3,3-dimethylallyl-(3)-, 3-methyl-3-ethyl-allyl-(3)-, butyne-, butyn-(1)-yl-(3)-, 3-methyl-butyn-(1)-yl-(3)-, 3-methyl-pentyn-(1)-yl-(3)-, 2-methoxyethyl-, 2-ethoxyethyl-, 3-methoxypropyl-, 3-ethoxypropyl-, 1-methoxy-butyl-(2)-, 1-n-propoxy-propyl-(2)-, methoxy-t-butyl- and ethoxy-t-butyl-carbamic acid chloride and corresponding carbamic acid bromides.

The first stage of the reaction, i.e., the decomposition, is carried out at not less than 25°C, preferably not less than 30°C, expediently from 35° to 100°C, and in particular from 40° to 95°C, above the boiling point of the N-alkylcarbamic acid halide, especially at from 120° to 160°C, under atmospheric or superatmospheric pressure, batchwise or, preferably, continuously. Organic solvents which are inert under the reaction conditions are used, advantageously those which are good solvents for the starting material I, boil at least 25°C, preferably at least 30°C, expediently from 35° to 100°C, and especially from 40° to 100°C, above the boiling point of the N-alkylcarbamic acid halide, and in particular boil at from 140° to 220°C, but are non-solvents or poor solvents for the hydrogen halide. Examples of possible solvents are aromatic hydrocarbons, e.g., ethylbenzene, o-, m- and p-xylene, isopropylbenzene and methylnaphthalene; halohydrocarbons, especially chlorohydrocarbons, e.g., tetrachloroethylene, n-amyl chloride, cyclohexyl chloride, 1,3-dichloropropane, dichlorobutane, chloronaphthalene, dichloronaphthalene, tetrachloroethane, pentachloroethane, o-, m- and p-difluorobenzene, 1,2-dichloroethane, chlorobenzene, fluorobenzene, bromobenzene, iodobenzene, o-, p- and m-dichlorobenzene, o-, p- and m-dibromobenzene, o-, m- and p-chlorotoluene, 1,2,4-trichlorobenzene, 1,10-dibromodecane and 1,4-dibromobutane; sulfoxides, such as dimethylsulfoxide; ethers, e.g., di-n-butyl ether, di-iso-amyl ether, diisopropyl ether, anisole, phenetole, cyclohexyl methyl ether, thioanisole and β,β'-dichlorodiethyl ether; esters, such as butyl acetate, methyl phthalate, methyl benzoate and phenyl acetate; nitrohydrocarbons, such as nitrobenzene, o-, m- and p-chloronitrobenzene and o-nitrotoluene; aliphatic or cycloaliphatic hydrocarbons, e.g., nonane, o-, m- and p-cymene, gasoline fractions boiling within the above boiling range, decalin, ligroin, 2,2,4-trimethylpentane, 2,2,3-trimethylpentane, 2,3,3-trimethylpentane and octane; ketones, such as acetophenone and cyclohexanone; and mixtures of the above. Suitable amounts of solvent to use are from 400 to 10,000% by weight, preferably from 600 to 1,500% by weight, based on the weight of the starting material I. Halohydrocarbons, especially aromatic halohydrocarbons, are preferred. The solvent, and the amount of solvent, are advantageously so chosen that the boiling point of the resulting solution of the starting material I corresponds to the decomposition temperature according to the invention stated above, i.e., is at least 25°C above the boiling point of starting material I.

The first stage of the reaction may be carried out as follows: a solution of the starting material in the solvent or solvent mixture is kept under reflux at the decomposition temperature for from 1 to 6 hours. The temperature of the reflux condenser is as a rule below the boiling point of the end product formed. The equipment used comprises columns with reflux fittings, as a rule distillation apparatuses with reflux condensers, and set to give total reflux of all the organic components of the reaction mixture.

After removing the hydrogen halide eliminated, the reaction mixture is passed to the 2nd stage, where the end product is isolated from the mixture, expediently by fractional distillation. Any desired distillation apparatuses may be used, e.g., sieve tray columns, Oldershaw columns, glass tray columns, bubble-cap tray columns, valve tray columns, thin layer evaporators and downflow distillation apparatuses. The second stage can be carried out under atmospheric or superatmospheric pressure, batchwise or, advantageously, continuously.

In a preferred embodiment, the process of the invention is carried out continuously. A suitable apparatus consists expediently of two, and advantageously of three, sections, namely the decomposition section and one or two distillation sections. The decomposition section consists of at least one stirred vessel equipped with a reflux unit; if several vessels are used, they are expediently linked by overflows, in the form of a cascade. An overflow is also an expedient way of linking the decomposition section to the first distillation section.

The attached drawing illustrates an advantageous design of the preferred embodiment. The solvent and the reaction mixture contained therein are recycled by a pump 1 from the boiler of the first distillation section 2 into the decomposition unit, where it is mixed, in a mixing device 5, with fresh carbamic acid halide 4 before entering the boiler of the decomposition unit 3. The amount of solvent circulated is adjusted to give the desired concentration with the continuously fed carbamic acid halide. The decomposition unit comprises reflux condensers 6 and the first distillation section comprises a column 7, from which the distillate is fed into the boiler of the second distillation section 8 via the connection 14. The end product is fractionally distilled through a column 10 into a receiver 11. Both column tops carry cooling devices 9 and the boilers of all parts of the installation are fitted with suitable stirrers 12. The overflows 13 and 14 respectively, connect the decomposition section and the second distillation section to the first distillation section. In this embodiment, from 95 to 100% of the theoretical amount of hydrogen chloride are, as a rule, released in the decomposition vessel and pass off through the reflux condenser.

In the preferred embodiment, the solution of the carbamic acid halide, preferably a carbamic acid chloride, is decomposed continuously in the boiler 3 of a distillation apparatus fitted with a reflux unit 6, and the decomposition mixture is passed via the overflow 13 into the boiler 2 of the first distillation column 7 and distilled there; the distillate, containing the crude end product, is passed via a connection 14 into the boiler 8 of the second distillation column 10, the pure end product is isolated by distilling it into a receiver 11 and the residual mixture in the second boiler 8 is recycled via an overflow 15, together with the residual mixture in the first boiler 2, to the boiler 3 of the decomposition section, fresh solvent 1 and starting material 4 being fed continuously into the circulated mixture.

Where the solutions of the starting material are very dilute, it is expedient not to take the decomposition of the carbamic acid halide to completion but instead to recycle the residual undecomposed starting material, together with the solvent, to the decomposition stage. In the first distillation section, the residual carbamic acid halide can be separated by distillation from the solvent, alongside the isocyanate formed.

In a particularly economical variant of the process, the solvent returned from the first distillation section is passed through a scrubber before reintroducing it into the boiler of the decomposition unit, and the off-gas from the decomposition section is simultaneously passed through this scrubber. This makes it possible substantially to absorb the very small proportion of isocyanate which has been entrained proportionately to its vapor pressure, with the hydrogen chloride evolved, and/or the very small proportion of carbamic acid chloride re-formed.

In the above preferred embodiment, each stage of the synthesis is carried out separately and is therefore easier to control. Only hydrogen chloride is distilled off in the decomposition unit; in the first distillation section, only the separation of the low-boiling isocyanate product and of the residual carbamic acid halide from the high-boiling solvent is carried out, requiring only a column of low separating efficiency, and finally, in the second distillation section, only a two-component separation, namely the separation of the carbamic acid halide from the isocyanate, is carried out. A practically pure isocyanate is obtained. Instead of using the pure starting material, mixtures of carbamic acid halide and isocyanate, or carbamic acid halide and the solvent, can also be employed continuously. This may be of advantage, e.g., if the synthesis of the carbamic acid chloride is carried out in the same solvent as that used in the process of the invention.

In an advantageous embodiment, a gas which is inert under the reaction conditions is passed through the reaction mixture during the decomposition and is removed from the mixture together with the hydrogen halide formed, e.g., in accordance with the process described in German Patent 2,411,452. It is possible to decompose the starting material and only to introduce the inert gas during the decomposition, e.g., 0.5 to 20 hours after the start of the decomposition of the starting material mixed with the solvent; however, it is more advantageous to introduce the inert gas from the very start, i.e., from the beginning of the decomposition. If the inert gas is circulated, it is preferably freed from hydrogen halide, for example by absorbing the latter in water to give hydrochloric acid, and dried, before re-entering the decomposition mixture. The inert gas may be passed through the reaction mixture intermittently or, preferably, continuously. The inert gas and hydrogen halide formed are discharged as off-gas through the reflux condenser. Suitable gases inert under the reaction conditions which may be used are rare gases, such as xenon, argon, neon and helium, alkanes such as methane, ethane, propane, 2,2-dimethylpropane, butane, pentane and isobutane, gaseous halohydrocarbons such as tetrafluoromethane, dichloromethane, chloromethane, bromomethane, hexafluoroethane, chloroethane and fluoroethane, gaseous organic compounds of inorganic elements such as tetramethylsilane, ethers, such as dimethyl ether and methyl ethyl ether and, preferably, nitrogen, oxygen, air and/or carbon dioxide, and mixtures of the above. In a suitable embodiment of the process, at least 80, preferably from 150 to 10,000, and in particular from 200 to 8,000 parts by volume of inert gas are used per part by weight of starting material I; under these conditions the amount of solvent is advantageously from 50 to 1,500% by weight, preferably from 80 to 900% by weight, based on the weight of starting material I. The preferred flow rate of the inert gas through the decomposition mixture is from 10 to 300, preferably from 30 to 240, parts by volume per hour per part by weight of starting material I.

The isocyanates which may be manufactured by the process of the invention are valuable starting materials for the manufacture of plant protection agents, pesticides, dyes, synthetic resins and plastics, hydrophobic agents for textiles, detergents, bleaches and adhesives. Their conversion to urethanes, e.g., for use as foams or high molecular weight coatings of great flexibility, or to ureas, is of particular importance. For details of their use, reference may be made to the above publications and to Ullmanns Encyklopedie der technischen Chemie, volume 9, pages 11, 12 and 404, and volume 17, page 204.

In the examples which follow, parts are by weight and bear the same relation to parts by volume as that of the kilogram to the liter.

EXAMPLE 1

A solution of 10 parts of isopropylcarbamic acid chloride (b.p. 85°C) in 90 parts of o-dichlorobenzene (b.p. 179°C) is heated to 130°C for 5 hours. 3.0 parts (virtually 100% of the theory) of hydrogen chloride gas are eliminated during this time. The reaction mixture is then distilled. 6.72 parts (96% of theory) of 99.6% pure isopropyl isocyanate boiling at 74°C are obtained.

EXAMPLE 2

A solution of 12 parts of isopropylcarbamic acid chloride in 88 parts of o-dichlorobenzene is introduced, at this rate per hour, into the boiler (3) of the decomposition section of an installation corresponding to the drawing and comprising a reflux column (6) and two distillation columns (7, 10), and is heated therein to 130°C. The hydrogen chloride formed passes through the cooled column (6) and is then absorbed in water. A total of 400 parts of o-dichlorobenzene are introduced initially, and after the circulation of the system has been set up, 0.5 part of solvent are introduced hourly to compensate for losses. The boiler of the first distillation column is filled, via an overflow, until it contains 150 parts of solution. The mixture is then circulated through the mixing and feed unit (5). In total, 90 parts of o-dichlorobenzene per hour are circulated. Under these conditions an average of 2 parts of isopropylcarbamic acid chloride are present at any time in the boiler of the decomposition section. The columns have cooling units (9) and all 3 sections of the installation have stirrers (2, 3, 8). 8.6 parts per hour of crude end product are passed into the boiler (8) of the second distillation column (10). 0.9 part of residues is returned to the circulation via the overflow (5), whilst 7.7 parts (92% of theory) of pure isopropyl isocyanate boiling at 74°C distill hourly into the receiver (11). 3.5 parts (98% of theory) of hydrogen chloride are eliminated per hour.

EXAMPLE 3

30 parts of methylcarbamic acid chloride (b.p. 93° to 94°C) are converted hourly analogously to Example 2. The solution of the starting material in o-dichlorobenzene remains constantly at 12 percent strength by weight in the decomposition section, the residence time being 3.5 hours. 17.96 parts (98.2% of theory) of methyl isocyanate boiling at 38.5°C are obtained hourly. 11.65 parts (99.5% of theory) of hydrogen chloride are eliminated per hour.

We claim:

1. A process for the manufacture of aliphatic isocyanates by thermal decomposition of aliphatic carbamic acid halides in the presence of inert organic solvents, wherein, in a first reaction stage, an aliphatic carbamic acid halide is decomposed at a temperature not less than 25°C above its boiling point in the presence of a solvent which boils at or above this temperature, during which stage the hydrogen halide formed is removed, and then, in a second stage, the aliphatic isocyanate formed is isolated from the decomposition mixture.

2. A process as claimed in claim 1 wherein:
   said aliphatic carbamic acid halide in said solvent is decomposed continuously in a first stage comprising the boiler of a first distillation apparatus fitted with a reflux unit,
   the decomposition mixture is passed via an overflow from said first stage into a second stage comprising the boiler of a second distillation apparatus in which the decomposition mixture is distilled through a distillation column from which the distillate containing the crude end product is conducted into another boiler for distillation through another distillation column from which the pure end product is isolated as distillate in a receiver, and
   the residual mixtures of the two boilers in the second stage are recycled to the decomposition boiler of the first stage, fresh solvent and starting material being continuously fed into the recycled mixture.

3. A process as claimed in claim 1, wherein a gas which is inert under the reaction conditions is passed through the reaction mixture during the decomposition and is separated from the mixture together with the hydrogen halide formed.

4. A process as claimed in claim 1, wherein the decomposition is carried out with organic solvents which are inert under the reaction conditions, which are good solvents for the starting material and boil at least 25°C above the boiling point of the aliphatic carbamic acid halide, but are non-solvents or poor solvents for the hydrogen halide.

5. A process as claimed in claim 1, wherein the decomposition is carried out at a temperature at least 30°C above the boiling point of the aliphatic carbamic acid halide.

6. A process as claimed in claim 1, wherein the decomposition is carried out at a temperature from 35° to 100°C above the boiling point of the aliphatic carbamic acid halide.

7. A process as claimed in claim 1, wherein the decomposition is carried out at a temperature from 40° to 95°C above the boiling point of the aliphatic carbamic acid halide.

8. A process as claimed in claim 1, wherein the decomposition is carried out at from 120° to 160°C.

9. A process as claimed in claim 1, wherein the amount of solvent used in the decomposition is from 400 to 10,000% by weight, based on starting material.

10. A process as claimed in claim 1, wherein the type and amount of solvent used in the decomposition is such that the boiling point of the resulting solution of the starting material I corresponds to the decomposition temperature.

11. A process as claimed in claim 1, wherein the decomposition is carried out with 150 to 10,000 parts by volume of inert gas per part of starting material and using from 50 to 1,500% by weight of solvent, based on starting material, and a flow rate of the inert gas, passed through the decomposition mixture, of from 10 to 300 parts by volume per hour per part of starting material.

* * * * *

UNITED STATES PATENT AND TRADEMARK OFFICE
CERTIFICATE OF CORRECTION

PATENT NO. : 3,969,389
DATED : July 13, 1976
INVENTOR(S) : Hans Urbach et al.

It is certified that error appears in the above-identified patent and that said Letters Patent are hereby corrected as shown below:

In Column 6, Line 3, delete " described in German Patent 2,411,452.... " and substitute -- described in German Patent 2,411,442.... --

Signed and Sealed this

Tenth Day of May 1977

[SEAL]

Attest:

RUTH C. MASON
Attesting Officer

C. MARSHALL DANN
Commissioner of Patents and Trademarks